United States Patent
Dunshee

Patent Number: 5,669,881
Date of Patent: Sep. 23, 1997

[54] VASCULAR INTRODUCER SYSTEM INCORPORATING INFLATABLE OCCLUSION BALLOON

[75] Inventor: Joyce Dunshee, Corona Delmar, Calif.

[73] Assignee: Baxter International Inc., Deerfield, Ill.

[21] Appl. No.: 370,705

[22] Filed: Jan. 10, 1995

[51] Int. Cl.$^6$ .................................................. A61M 29/00
[52] U.S. Cl. ........................... 604/164; 604/167; 604/99
[58] Field of Search .......................... 604/96, 97, 99, 604/102, 107, 174, 175, 280, 283, 284

[56] References Cited

U.S. PATENT DOCUMENTS

| | | |
|---|---|---|
| 4,323,071 | 4/1982 | Simpson et al. |
| 4,464,175 | 8/1984 | Altman et al. .................. 604/167 X |
| 4,776,347 | 10/1988 | Matthews ......................... 604/99 X |
| 4,781,681 | 11/1988 | Sharrow et al. |
| 4,793,351 | 12/1988 | Landman et al. ................ 604/99 X |
| 4,850,953 | 7/1989 | Haber et al. ..................... 604/96 X |
| 4,857,062 | 8/1989 | Russell ............................. 604/167 X |
| 4,911,163 | 3/1990 | Fina . |
| 5,045,061 | 9/1991 | Seifert et al. . |
| 5,061,273 | 10/1991 | Yock . |
| 5,080,654 | 1/1992 | Picha et al. ..................... 604/167 |
| 5,100,381 | 3/1992 | Burns . |
| 5,158,540 | 10/1992 | Wijay et al. .................... 604/96 X |
| 5,224,933 | 7/1993 | Bromander ...................... 604/99 |
| 5,267,982 | 12/1993 | Sylvonowicz . |
| 5,273,534 | 12/1993 | Knoepfler ......................... 604/96 |
| 5,295,969 | 3/1994 | Fischell et al. ................... 604/167 X |
| 5,300,034 | 4/1994 | Behnke et al. .................... 604/167 |
| 5,324,262 | 6/1994 | Fischell et al. . |
| 5,324,271 | 6/1994 | Abiuso et al. ..................... 604/167 |
| 5,330,451 | 7/1994 | Gabbay . |
| 5,338,299 | 8/1994 | Barlow . |
| 5,344,399 | 9/1994 | DeVries . |
| 5,409,463 | 4/1995 | Thomas et al. .................... 604/167 |
| 5,464,394 | 11/1995 | Miller et al. . |

FOREIGN PATENT DOCUMENTS

| | | |
|---|---|---|
| 0 339 501 | 11/1989 | European Pat. Off. . |
| 2645-750-A | 10/1990 | France . |
| 3823-144-A | 1/1990 | Germany . |
| WO 87/07510 | 12/1987 | WIPO . |
| WO 92/12755 | 8/1992 | WIPO . |
| WO 94/02197 | 2/1994 | WIPO . |

Primary Examiner—Sam Rimell
Attorney, Agent, or Firm—Stetina & Brunda; Raymond Sun

[57] ABSTRACT

A vascular introducer comprising a pliable tube having an occlusion balloon mounted thereon to occlude or block blood flow through a blood vessel into which the introducer is inserted. A valving apparatus is associated with the lumen of the introducer to prevent blood or other fluids from backflowing out of the proximal end of the introducer. A dilator, having a tapered distal portion, is insertable through the introducer to dilate a puncture tract into which the introducer is inserted. The introducer may also provide a gripping apparatus for gripping and holding a dilator, catheter, scope or other object inserted through the lumen of the introducer.

60 Claims, 4 Drawing Sheets

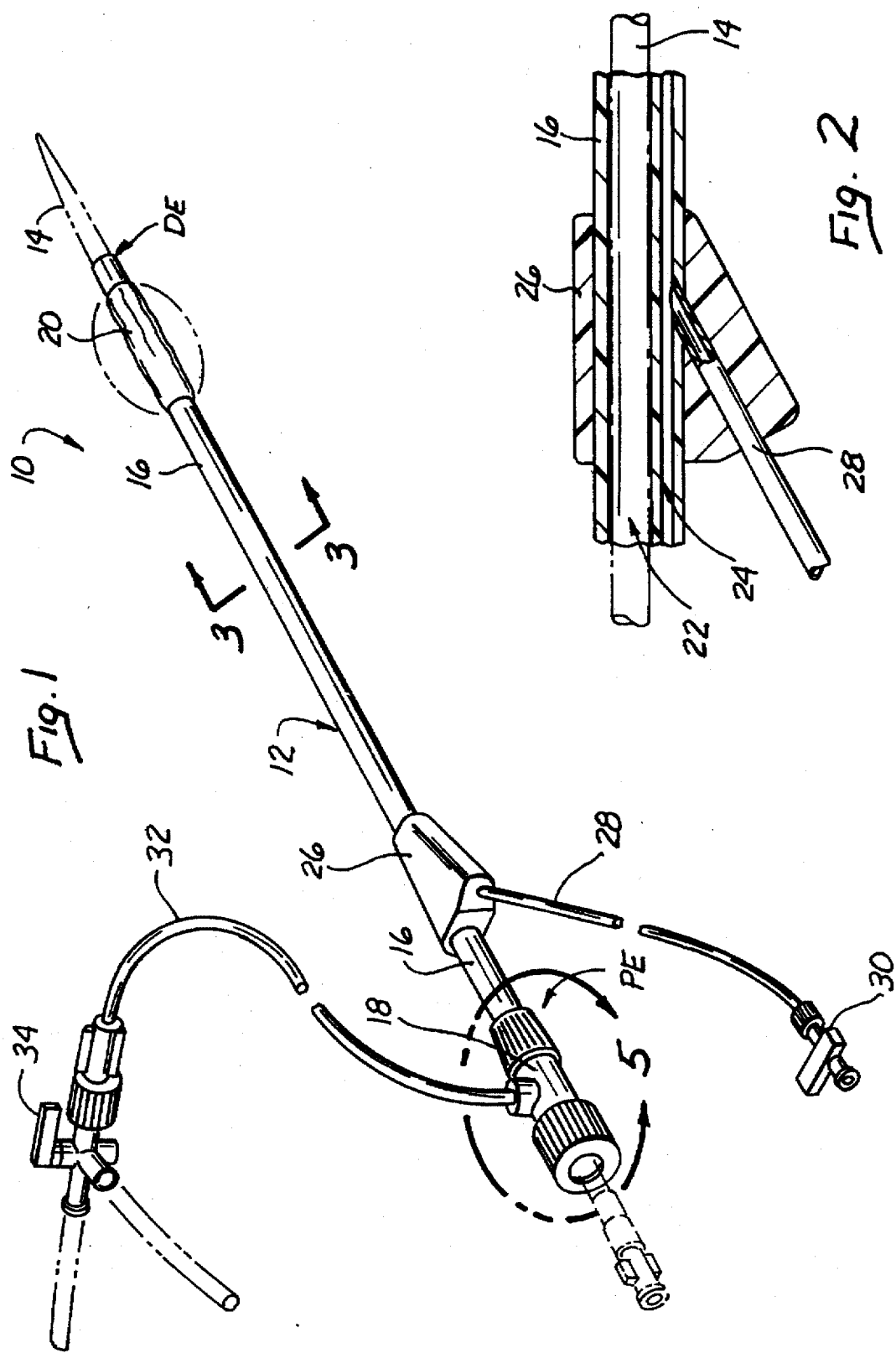

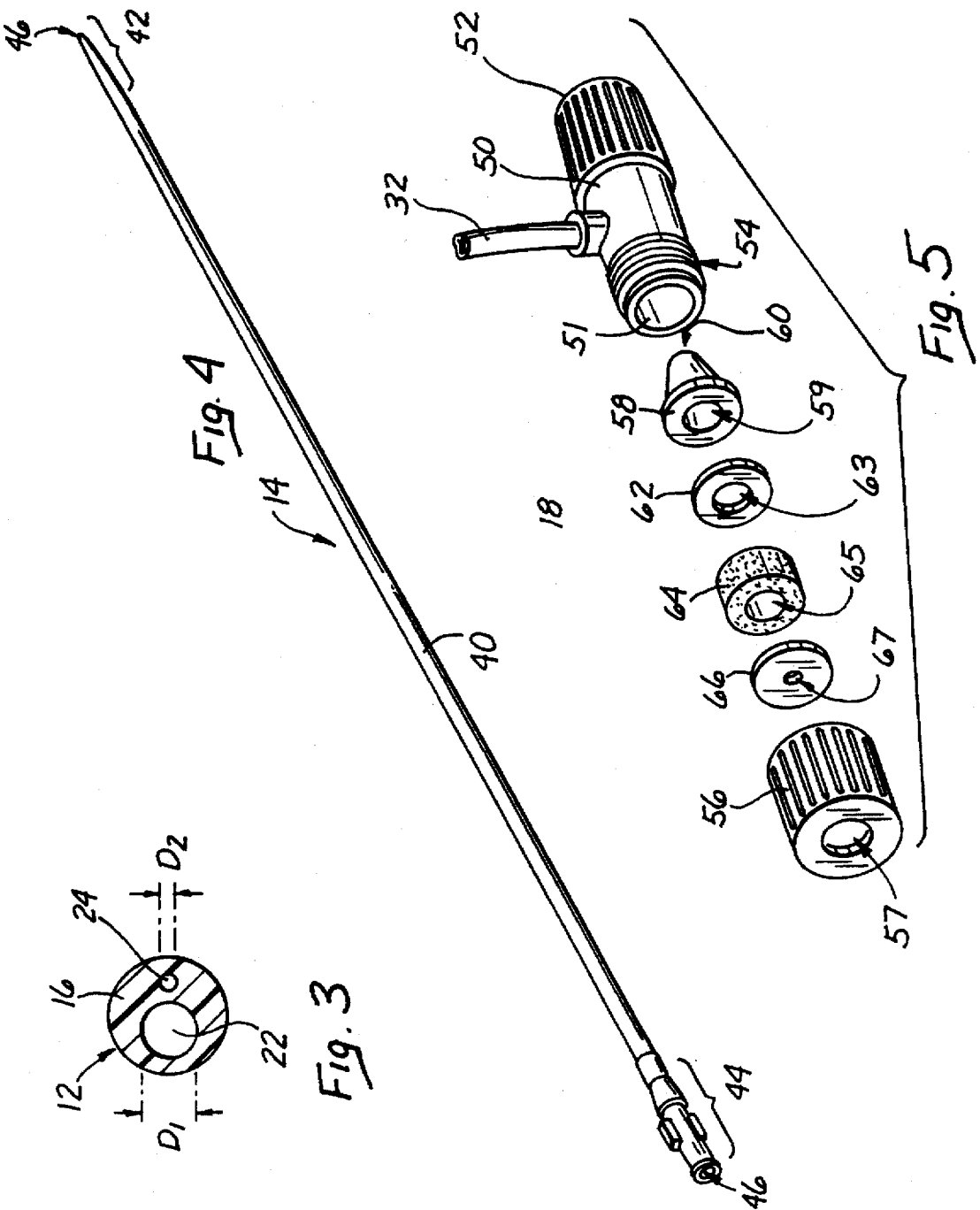

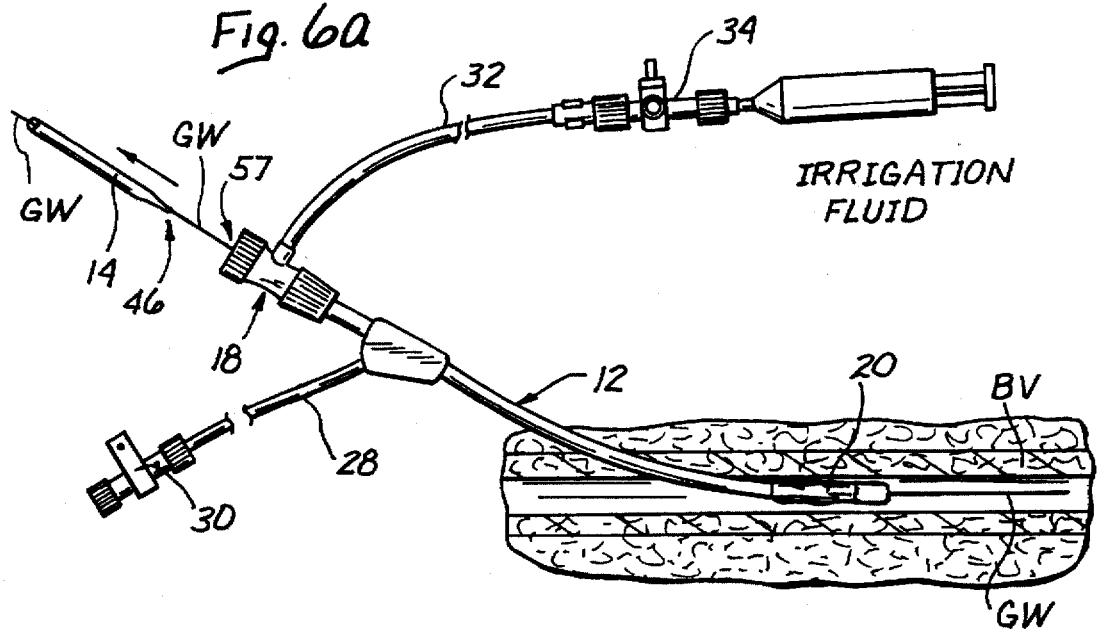
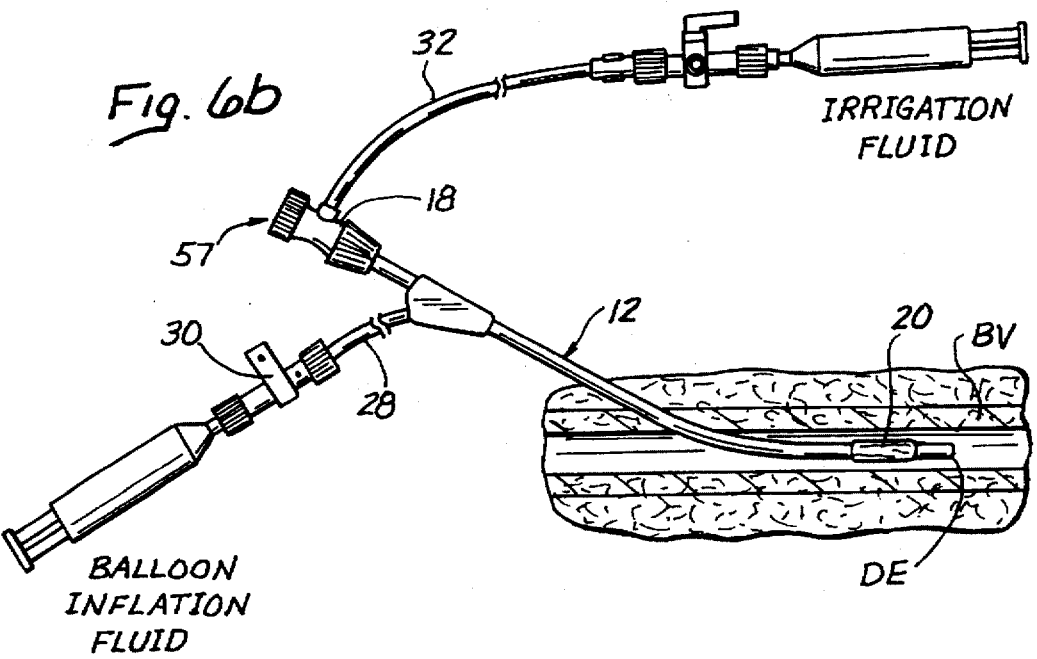

5,669,881

VASCULAR INTRODUCER SYSTEM INCORPORATING INFLATABLE OCCLUSION BALLOON

FIELD OF THE INVENTION

BACKGROUND OF THE INVENTION

In modern clinical medical practice, many types of catheters, scopes and other devices are introduced, percutaneously, into blood vessels. Clinical procedures wherein catheters or scopes are introduced into blood vessels include: diagnostic cardiac catheterization, percutaneously transluminal balloon angioplasty (PCTA), embolectomy, atherectomy, etc.

One standard method utilized for percutaneous insertion of catheters, scopes or other devices into blood vessels is known as the "Seldinger Technique". In accordance with the Seldinger Technique, a hollow bore needle is initially inserted into a blood vessel (e.g., femoral artery, brachial artery, etc . . . ) and a guidewire is subsequently advanced through the lumen of the needle into the blood vessel. The needle is then retracted, leaving the guidewire in place. Thereafter, a tapered dilator, having a guidewire lumen extending therethrough, is inserted through a relatively large diameter introducer sheath such that the tapered distal end of the dilator protrudes out of and beyond the distal end of the sheath. The introducer sheath/dilator combination is then advanced over the prepositioned guidewire such that the distal end of the dilator causes the original needle puncture tract to dilate, thereby allowing passage of the relatively large diameter introducer into the blood vessel. After the distal end of the introducer has been advanced into the blood vessel the tapered dilator is withdrawn and removed, leaving the introducer sheath in place within the blood vessel. The desired catheter, scope or other device is then passed through the lumen of the introducer sheath, and advanced through the vasculature, to its intended location within the cardiovascular anatomy.

Recently developed endoluminal operative procedures (e.g., angioscopy, embolectomy, endoluminal graft placement, stent placement etc . . .) sometime necessitate or render desirable, the occlusion of blood flow through the blood vessel into which the introducer is inserted. The standard vascular introducers of the prior art have not been equipped with occlusion balloons or other means for blocking blood flow through the blood vessel into which they are inserted. Thus, in instances where blockage of blood flow at or near the distal end of the introducer sheath is desirable, it is typically necessary to pass a separate balloon catheter or other occlusion apparatus into the blood vessel to effect the desired blockage of blood flow through the blood vessel. Examples of balloon catheters of the prior art are well known, and include those disclosed in the following United States and foreign patents and patent publications: U.S. Pat. No. 5,344,399 (DeVries); U.S. Pat. No. 5,330,451, (Gabbay); U.S. Pat. No. 5,324,262, (Fischell et al.); U.S. Pat. No. 5,338,299, (Barlow); U.S. Pat. No. 4,323,071, (Simpson et al.); U.S. Pat. No. 4,781,681, (Sharrow et al.); U.S. Pat. No. 4,911,163, (Fina); U.S. Pat. No. 5,045,061, (Seifert et al.); U.S. Pat. No. 5,061,273, (Yock); U.S. Pat. No. 5,100,381, (Burns); U.S. Pat. No. 5,267,982, (Sylvonowicz); Foreign Patent Nos.: DE 3823-144-A(Deutschland), (Ludwig); 0 339 501 (European), (Muti); PCT WO 94/02197 (Muni et al.); PCT 2645-750-A (French), (Hono); PCT WO 87/07510, (Bazzichelli); PCT WO 92/12755, (Shturman).

Recognizing that it is sometimes desirable to occlude or block blood flow through the blood vessel into which the introducer sheath is inserted, one prior art apparatus, published as French Patent Application FR 2645-750-A entitled "Inflatable Arterial Plug-Comprises Balloon Which Allows Blood Flow to be Stopped During Insertion of Instrument", has described a vascular introducer system which incorporates an inflatable balloon for blocking blood flow through the blood vessel into which the introducer system is inserted. A first embodiment of an introducer device described in FR 2645-750-A is an elongate tube having a balloon mounted on the outer surface of the tube, near the distal end thereof. A detachable cap or plug is positioned on the proximal end of the introducer tube. The detachable cap or plug must be removed in order to permit insertion of a scope, catheter or other device through the introducer tube. FR 2645-750-A does not disclose or describe the provision of a valving apparatus capable of preventing backflow and leakage of blood out of the proximal end of the introducer tube when the detachable cap or plug has been removed. Furthermore, FR 2645-750-A does not disclose or describe the provision of a gripping apparatus capable of grasping and stabilizing a scope, catheter or other elongate device which has been inserted through the introducer tube.

FR 2645-750-A also describes a second embodiment wherein the above-described balloon-equipped introducer tube is inserted through a prepositioned outer introducer tube, thereby forming a system which includes an inner tube (i.e., the above-described introducer having a balloon) and separate outer tube. The outer tube is devoid of any inflatable occlusion balloon. The outer tube may incorporate a valving apparatus to permit blood to be vented outwardly, through a space which exists between the outer surface of the inner tube and the inner surface of the outer tube, to prevent-over pressurization of the blood vessel in the event that the occlusion balloon of the inner tube becomes blocked or otherwise prevented from timely deflation.

Although the system described in FR 2645-750-A is purportedly usable to obturate blood flow within a blood vessel when an angioscope or other device is inserted through the inner introducer tube, it is to be recognized that the inner introducer tube lacks any valving mechanism to prevent leakage of blood or to hold the angioscope or other device in place. Furthermore, the utilization of two separate (e.g., inner and outer) introducer tubes as described in the second embodiment of FR 2645-750-A may increase the cost and complexity of the system and may add unnecessary complexity to some or all clinical applications of the system.

There remains a need in the art for the development of a single-tube vascular introducer capable of facilitating the insertion of various angioscopes, catheters and devices while preventing leakage or backflow of blood through the introducer, which also incorporates an inflatable occlusion balloon capable of blocking the flow of blood through the blood vessel into which the introducer is inserted.

SUMMARY OF THE INVENTION

The present invention provides a vascular introducer which generally comprises the combination of a) a tubular introducer sheath, b) an occlusion balloon on the outer surface of the introducer sheath to occlude blood flow through a blood vessel into which the introducer sheath is inserted, and c) a hemostasis valving apparatus to prevent backflow or leakage of blood or other fluid out of the proximal end of the sheath with or without an elongate object (e.g., dilator, catheter, scope) inserted therethrough. The introducer apparatus comprises an elongate, pliable tubular body which is insertable into the lumen of a blood vessel. An inflatable occlusion balloon is formed or mounted on the outer surface of the tubular body such that, when the tubular body is inserted into a blood vessel, the occlusion balloon will reside within the lumen of the blood vessel. A balloon inflation tube or lumen extends through at least a portion of the introducer body to permit infusion of balloon inflation fluid into the balloon. A valving apparatus is associated with the working lumen of the introducer to prevent blood or other fluid from backflowing out of the proximal end of the introducer. In addition, to the valving apparatus, the introducer may include a gripping apparatus for gripping or holding a dilator, catheter, scope or other object which has been inserted through the working lumen of the introducer.

Further in accordance with the invention, the introducer apparatus may include an elongate dilator member insertable through the working lumen of the introducer apparatus. A tapered distal portion of the dilator member protrudes beyond the distal end of the introducer to dilate a puncture tract or other opening through which the introducer is inserted.

Still further in accordance with the invention, the introducer apparatus of the forgoing character may be manufactured using a dual-lumen tube having a relatively large working lumen and a relatively small balloon inflation lumen extending longitudinally therethrough. A balloon inflation side tube may be inserted into the balloon inflation lumen, and extend outwardly therefrom to facilitate passage of balloon inflation fluid through the balloon inflation lumen and into the occlusion balloon. A fluid infusion side tube may be inserted into the working lumen, and may extend outwardly therefrom, to facilitate infusion/aspiration fluid through the working lumen.

Further objects and advantages of the invention will become apparent to those skilled in the art upon reading and understanding of the following detailed description, and consideration of the accompanying drawings.

BRIEF DESCRIPTION OF THE DRAWINGS

FIG. 1 is a perspective view of a preferred vascular introducer system of the present invention.

FIG. 2 is a longitudinal sectional view of a portion of the introducer system shown in FIG. 1.

FIG. 3 is a cross-sectional view through line 3—3 of FIG. 1.

FIG. 4 is a perspective view of the preferred dilator component of the introducer system shown in FIG. 1.

FIG. 5 is an exploded view of the proximal valving/gripping assembly incorporated in the vascular introducer system of FIG. 1.

FIG. 6a–6c is a step-wise illustration of a method by which the vascular introducer system of the present invention is utilized to facilitate percutaneous insertion and use of an angioscope, catheter or other device.

DETAILED DESCRIPTION OF THE PREFERRED EMBODIMENT

Figure 6C:
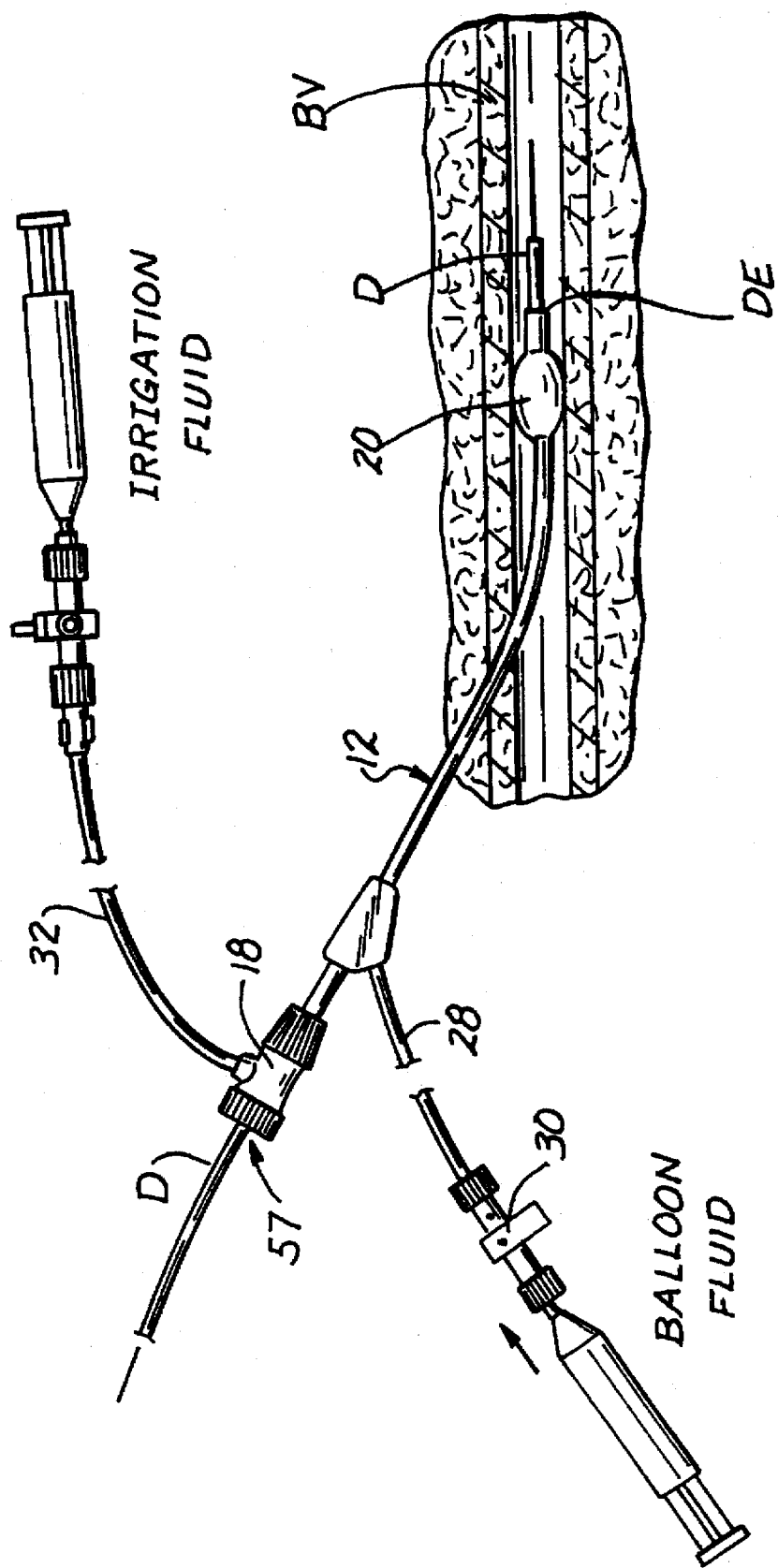

The following detailed description and the accompanying drawings are provided for purposes of describing and illustrating a presently preferred embodiment of the invention only, and are not intended to limit the scope of the invention in any way.

With reference to the appended drawings, the balloon introducer system 10 of the present invention generally comprises a balloon introducer device 12 and a tapered dilator 14 which is positionable longitudinally through the introducer device 12.

The preferred balloon introducer device 12 comprises an elongate pliable lumen body 16 having a first main lumen 22 and a second balloon inflation lumen 24 extending longitudinally therethrough. An inflatable balloon 20 is mounted about the outer surface of the introducer body 16, near the distal end DE thereof. The balloon inflation lumen 24 opens distally into the interior of the balloon 20 such that balloon inflation fluid passed through the balloon inflation lumen 24 will flow into, and inflate, balloon 20. A balloon inflation side tube 28, having a slide valve 30, is connected to the balloon inflation lumen 24 to facilitate inflation and deflation of the balloon 20.

A side tube 32, having a stop cock 34, is connected to the main lumen 22 of the introducer device 12 to facilitate infusion of fluid (e.g., 0.9% NACL; 5% dextrose in water or other irrigation fluid) through the main lumen 22 of the introducer device 12.

A proximal valving/gripping assembly 18 is mounted on the proximal end PE of the introducer body 16. The valving/gripping assembly 18 preferably incorporates a hemostasis valve or check valve capable of preventing blood or other fluid from backflowing out of the proximal end opening 57 of the introducer device 12. Additionally, the valving/gripping assembly 18 preferably incorporates a gripping system capable of radially grasping the dilator 14, angioscope, catheter or any other device which has been inserted into the main lumen 22 of the introducer device 12. In this regard, the valving/gripping assembly 18 may be utilized to affix the dilator 14, angioscope, catheter or other device in a substantially stationary longitudinal position within the introducer device 12.

The preferred dilator 14 comprises an elongate member having a progressively narrowed or tapered distal portion 42, a proximal syringe-connection hub 44 and a hollow guidewire lumen 46 which extends longitudinally therethrough. The length of the dilator 14 is such that, when the dilator is inserted through the main lumen 22 of the introducer device 12, the tapered distal portion 42 of the dilator will protrude out of and beyond the distal end DE of the introducer body 16. As described herebelow, this preferred positioning of the dilator 14 within the main lumen 22 of the introducer device 12 facilitates insertion of the introducer device 12 into a blood vessel using the Seldinger Technique.

A preferred construction of the introducer device 12 is shown, in part, in FIG. 2. With reference to FIG. 2, the pliable body 16 of the introducer device 12 may comprise an extruded plastic tube having a substantially round or cylindrical main lumen 22 said lumen 22 having a first diameter D1 preferably of approximately 1–10 French. Also, there is provided a substantially round or cylindrical balloon inflation lumen 24 of a smaller second diameter D2 preferably approximately 0.010–0.020 inches. The balloon inflation side tube 28 is passed through the side wall of the introducer body 16, near the proximal end thereof, and is joined with the balloon inflation lumen 24 at that point, such that balloon inflation fluid may freely flow from the balloon inflation side tube 28, through the balloon inflation lumen 24 and into the balloon 20. Also, the balloon inflation fluid may be withdrawn therethrough when it is desired to deflate the balloon 20.

A plastic encasement member 26 is molded, fused or otherwise affixed about the outer surface of the introducer device 12, in the region where the introducer inflation side tube 28 enters the introducer body 16. Such encasement member 26 serves to secure the balloon inflation side tube 26 to the introducer body 16 and also forms a graspable surface which may be utilized for hand-holding of the introducer device 12 or gripping of the introducer device 12 by a fixture, clamp, or other apparatus.

It will be appreciated that various types of valving/ gripping assemblies 18 may be positioned on the proximal end of the introducer body 16. One representative type of valving/gripping apparatus 18 is specifically shown in FIG. 5. With reference to FIG. 5, such valving/gripping apparatus 18 comprises a rigid tubular body member 50 having a hollow bore 51 extending longitudinally therethrough, and having irrigation side tube 32 connected thereto such that irrigation fluid flowing through side tube 32 will pass into the inner bore 51 of the tubular member 50. A distal connector apparatus 52 is positioned on the distal end of the tubular body 50 to receive and connect the tubular body 50 to the proximal end of the introducer body 16 such that the hollow bore 51 of the tubular member 50 is connected to and continuous with only the main working lumen 22 of the introducer body 16. A hemostasis valving member 58, having a self-closing slit aperture 60 is sized and configured to partially insert into, and mount within the proximal opening of the hollow bore 51 of the tubular member 50. A first washer 62 is positionable in contact with the proximal end of the hemostasis valving member 58 and incorporates a central aperture 63 sized and configured to align with the central aperture 59 of the hemostasis valving member 58. A compressible gripping ring 64 having a central aperture 65 is positioned in abutment with the proximal side of the first washer 62. When in its non-compressed state the central aperture 65 of the compressible ring 64 is substantially equal in size to, and is in alignment with, the central apertures 63 and 59 of the first washer 62 and hemostasis valving member 58. A second washer 66 is positioned on the proximal side of the compressible ring 64. The second washer 66 has a central aperture 64 which is preferably smaller in diameter than the non-compressed central aperture 65 of the gripping ring 64, but which is sufficiently large to accommodate and permit passage therethrough of the intended angioscope, catheter or other device to be inserted through the introducer device 12. A proximal end cap 56, having proximal opening 57 formed therein, is threadably advanceable onto the proximal end of the tubular member 50 so as to entrap and hold the hemostasis valving member 58, first washer 62, gripping ring 64 and second washer 66 therebetween. When no object is inserted through the device 12 the self-closing aperture or slit opening 60 of the hemostasis valving member 58 will remain closed to prevent blood or other fluid from backflowing out of the proximal opening 57 of end cap 56. Thereafter, when a dilator 14, angioscope, catheter or other device is inserted through device 12, it will pass through the proximal opening 57, through central apertures 67, 65, 63, 59, through self-sealing aperture 60, through the bore 51 of tubular member 50, and through the main working lumen 22 of the introducer body 16. Additionally, to stabilize, hold and form a fluid tight seal against the dilator 14, angioscope, catheter or other device, the prOximal end cap 56 may be tightened onto the threaded distal portion 54 of the tubular member 50, thereby compressing the gripping ring 64 between first and second washers 62, 66. Such compression of the gripping ring 64 will cause the flowable or elastomeric material of the gripping ring 64 to flow or deform inwardly, causing the central aperture 65 of the gripping ring 64 to become smaller as to radially compress against the outer surface of the dilator 14, angioscope, catheter or other device which has been inserted therethrough. In this regard, the preferred valving/gripping assembly 18 is operative to grasp and hold the dilator 14, angioscope, catheter or other device which has been inserted into or through the introducer device 12. Also, in this regard, the valving/gripping assembly 18 forms a fluid tight seal against the outer surface of any dilator 14 angioscope, catheter or other elongate object inserted therethrough to prevent backflow or leakage of body fluids around such object.

The balloon 20 is preferably mounted within 1 cm of the distal end DE of the introducer body 16 and is preferably configured such that, when fully inflated, the outer diameter of the balloon 20 is the same as or larger than the luminal diameter of the blood vessel into which the introducer device 12 has been inserted so as to fully occlude and block off blood flow through the lumen of the blood vessel. Such inflation of the balloon 20 is facilitated by attaching a syringe to the balloon inflation side tube 28, opening slide valve 30, and utilizing the syringe to inject the desired amount of balloon inflation fluid into the balloon 20. Thereafter, the slide valve 30 may be closed to entrap and hold the balloon inflation fluid with the balloon 20. When it is desired to deflate the balloon 20, the slide valve 30 will be opened, and the syringe will be utilized to withdraw the previously-infused balloon inflation fluid to fully deflate the balloon 20.

Prior to or after inflation of the balloon 20, various fluids may be infused through fluid infusion side tube 32, and through the working lumen 22 of the introducer device 12. In this regard, it will be appreciated that after the occlusion balloon 20 is inflated, it may be desirable to infuse clear fluids into a blood vessel downstream of the occlusion balloon 20 to displace any blood contained therein, and to provide a clear fluid environment within which an angioscope may be utilized to view the surrounding walls of the blood vessel. Such infusion of fluid will be typically accomplished by opening the stop cock 34 to the appropriate side arm thereof, and utilizing an attendant pressurized fluid delivery system or syringe to infuse the desired fluid through the side tube 32, through working lumen 22 and out of the open distal end DE of the introducer sheath. When an angioscope, catheter or other device is inserted through the introducer device 12, it is desirable that a small space remain between the outer surface of the angioscope, catheter or other device and the inner wall of the working lumen 22 of the introducer device so as to permit the desired irrigation fluid to freely flow around the through-positioned angioscope, catheter or other device and out of the distal end DE of the introducer body 16.

Method of Use

The preferred method by which the balloon introducer system 10 of the present invention may be utilized is shown schematically in FIGS. 6a–6c.

FIG. 6a

After the introducer device 12 and dilator 14 have been conjointly inserted into the blood vessel BV over prepositioned guidewire GW, the dilator 14 is withdrawn in the proximal direction and removed. The guidewire GW may be allowed to remain, or may also be removed.

FIG. 6b

After the dilator 14 or dilator/guidewire combination 14/GW has been withdrawn and removed, the proximal valving/gripping assembly 18 serves to prevent blood from backflowing out of the proximal opening 57 of the introducer device 12. This permits the introducer device 12 to remain inserted into a blood vessel, without any dilator 14, scope catheter or other elongate object inserted therethrough, for a desired period of time without concerns of blood leakage from the lumen of blood vessel BV. A syringe S1 mounted on the fluid infusion side tube 32 may be utilized to withdraw a small amount of blood to make certain that the distal end DE of the introducer device 12 is appropriately positioned within the lumen of the blood vessel BV. Thereafter, heparinized irrigation fluid, or any other desired fluid, may be infused through the main lumen of the introducer device 12 to displace any residual blood contained within the blood vessel, immediately distal to the occlusion balloon 20.

When it is desired, an angioscope, catheter or other device D is inserted through the proximal end opening 67 of the introducer device 12, through the introducer device 12 and out of the open distal end DE of the introducer body 16. The device so inserted may comprise any suitable type of device, including but not necessarily limited to devices which incorporate multiple telescoping members such as angioscopes currently used in the art. FIG. 6c shows a device which incorporates such multiple telescoping members, as illustrated extending out of and beyond the distal end DE of the introducer device 12.

FIG. 6c

When it is desired to occlude blood flow through the blood vessel BV, a syringe containing balloon inflation fluid is connected to slide valve 30, slide valve 30 is opened, and the desired balloon inflation fluid is injected through balloon inflation side tube 28, through the balloon inflation lumen 24 of the introducer device 12 and into the balloon 20. Thereafter, the slide valve 30 may be closed to entrap and hold the desired amount of balloon inflation fluid within the balloon 20. Clear irrigation fluid may then be infused through irrigation fluid side tube 32, through the introducer device 12, and out of the distal end DE thereof so as to displace blood contained within the lumen of the blood vessel BV downstream of the occlusion balloon 20, thereby providing a clear fluidic environment within which the angioscope, catheter or other device D may be operated.

Alternatively, in other applications, such as suction embolectomy, or embolectomy procedureS, it will be unnecessary to develop a clear fluidic environment downstream of the balloon 20, and the inflation of the occlusion balloon 20 will be desirable only for purposes of closing off the blood flow to the region wherein the endoluminal operative procedure is being performed.

It is to be appreciated that the invention has been described hereabove with reference to certain selected, presently preferred embodiments, and no effort has been made to exhaustively describe and illustrate all possible embodiments in which the invention may take physical form, or be methodologically practiced. Indeed, numerous modifications, additions, deletions and alterations may be made to the above-described embodiments without departing from the intended spirit and scope of the invention. Accordingly, it is intended that all such additions, deletions, modifications and alterations be included within the scope of the following claims.

What is claimed is:

1. A vascular introducer apparatus having an occlusion balloon, said apparatus comprising:

an elongate pliable introducer body insertable into a blood vessel, said introducer body having a proximal end, a distal end, an outer surface and a working lumen extending longitudinally therethrough;

an inflatable occlusion balloon mounted on the outer surface of the introducer body;

a balloon inflation lumen extending through at least a portion of the introducer body to permit infusion of inflation fluid into said balloon;

a hemostasis valving apparatus associated with the working lumen of said introducer apparatus, said valving apparatus comprising a self sealing passageway which will become fully closed and prevent fluid from backflowing out of the proximal end of said working lumen when no elongate object is inserted therethrough, and which will permit insertion of an elongate object through said valving apparatus and through the working lumen of the introducer;

said valving apparatus including a sealing apparatus to seal against a elongate object inserted through said valving apparatus to thereby prevent fluid from backflowing out of the proximal end of said working lumen when an elongate object is inserted therethrough; and a dilator member insertable through the working lumen of the introducer apparatus, said dilator member having a tapered distal portion which extends beyond the distal end of the introducer apparatus, and said dilator member comprising a guidewire lumen extending longitudinally therethrough.

2. The apparatus of claim 1 wherein said introducer body is a dual lumen tube having said working lumen and said balloon inflation lumen extending longitudinally therethrough.

3. The apparatus of claim 2 wherein a balloon inflation side tube is connected to, and extends outwardly from, said balloon inflation lumen, to permit infusion of balloon inflation fluid through said balloon inflation lumen.

4. The apparatus of claim 3 further comprising:

a valving apparatus on said balloon inflation side tube.

5. The apparatus of claim 4 wherein said valving apparatus is a slide valve having a Leur connector formed thereon to permit attachment of a syringe thereto.

6. The apparatus of claim 1 wherein said introducer body has a length of less than 30 cm.

7. The apparatus of claim 1 wherein said introducer body has a length of approximately 20 cm.

8. The apparatus of claim 1 wherein said introducer body is substantially cylindrical, and has an outer diameter of 3–12 French.

9. The apparatus of claim 6 wherein said working lumen is substantially cylindrical and has a diameter of approximately 1–10 French.

10. The apparatus of claim 1 wherein said balloon inflation lumen is substantially cylindrical and has a diameter of 0.010–0.020 inches.

11. The apparatus of claim 1 wherein said introducer body comprises an extruded dual-lumen plastic tube having said main lumen and said balloon inflation lumen formed therein in substantially side-by-side relation to one another.

12. The apparatus of claim 11 further comprising a balloon inflation side tube connected to and extending outwardly from said balloon inflation lumen to permit infusion of balloon inflation fluid therethrough.

13. The apparatus of claim 11 further comprising:

a fluid infusion side tube connected to and extending outwardly from said main lumen to permit infusion of fluid therethrough.

14. The apparatus of claim 1 wherein said introducer body is formed of material selected from the group consisting of:

a) Fluropolymer b) Polyurethane c) Vinyl d) Nylon.

15. The apparatus of claim 1 wherein said balloon comprises a cylindrical elastic balloon having a proximal end, a distal end, and a cylindrical mid-portion extending between the proximal and distal ends thereof, said cylindrical elastic balloon being affixed to the outer surface of said introducer body such that balloon inflation fluid may be instilled between said introducer body and the mid-portion of said balloon to cause the mid-portion of said balloon to inflate annularly about said introducer body.

16. The apparatus of claim 15 wherein the mid-portion of said balloon is configured such that, when fully inflated, said balloon has an annular outer diameter of approximately 10–50 cm.

17. The apparatus of claim 1 wherein said valving apparatus is incorporated into a valving assembly mounted on the proximal end of said introducer body.

18. The apparatus of claim 17 wherein said valving assembly comprises:

said valving apparatus;

an end cap mounted over said valving apparatus, said end cap having a proximal opening formed therein, the proximal opening of said end cap being in alignment with the self-sealing passageway of said valving apparatus such that an elongate object may be inserted through said proximal opening, of the end cap, through the self-sealing passageway of said valving apparatus, and through the main lumen of said introducer body.

19. The apparatus of claim 18, wherein said valving assembly further comprises:

a gripping apparatus operative to frictionally engage and hold an elongate object inserted through said introducer apparatus.

20. The apparatus of claim 19 wherein said gripping apparatus comprises:

a compressible gripping ring mounted in alignment with the proximal opening of said end cap such that, when said end cap is tightened, said gripping ring will be compressed.

21. The apparatus of claim 20 further comprising:

first and second rigid washers positioned on opposite sides of said gripping ring such that when said end cap is tightened, said gripping ring will be compressed between said washers.

22. The apparatus of claim 1 wherein said dilator member comprises:

an elongate member having a proximal end, a distal end, and an outer surface, said tapered distal region being immediately adjacent said distal end thereof;

said dilator member being insertable through said valving apparatus and through the working lumen of the introducer apparatus such that the tapered distal portion of the dilator protrudes beyond the distal end of the introducer apparatus and the valving member forms a seal against the outer surface of the dilator member.

23. The apparatus of claim 22 wherein said dilator member has a guidewire lumen extending longitudinally therethrough.

24. A vascular introducer apparatus having an occlusion balloon, said apparatus comprising:

an elongate pliable introducer body insertable into a blood vessel, said introducer body having a proximal end, a distal end, an outer surface and a working lumen extending longitudinally therethrough;

an inflatable occlusion balloon mounted on the outer surface of the introducer body;

a balloon inflation lumen extending through at least a portion of the introducer body to permit infusion of inflation fluid into said balloon;

a hemostasis valving apparatus associated with the working lumen of said introducer apparatus, said valving apparatus comprising a self sealing passageway which will become fully closed and prevent fluid from backflowing out of the proximal end of said working lumen when no elongate object is inserted therethrough, and which will permit insertion of an elongate object through said valving apparatus and through the working lumen of the introducer;

said valving apparatus including a sealing apparatus to seal against a elongate object inserted through said valving apparatus to thereby prevent fluid from backflowing out of the proximal end of said working lumen when an elongate object is inserted therethrough; and wherein said valving apparatus is incorporated into a valving assembly mounted on the proximal end of said introducer body, said valving assembly comprising:

i. an end cap mounted over said valving apparatus, said end cap having a proximal opening formed therein, the proximal opening of said end cap being in alignment with the self-sealing passageway of said valving apparatus such that an elongate object may be inserted through said proximal opening of the end cap, through the self-sealing passageway of said valving apparatus, and through the main lumen of said introducer body; and ii. a gripping apparatus operative to frictionally engage and hold an elongate object inserted through said introducer apparatus, said gripping apparatus comprising a compressible gripping ring mounted in alignment with the proximal opening of said end cap such that, when said end cap is tightened, said gripping ring will be compressed, and first and second rigid washers positioned on opposite sides of said gripping ring such that when said end cap is tightened, said gripping ring will be compressed between said washers.

25. The apparatus of claim 24 wherein said introducer body is a dual lumen tube having said working lumen and said balloon inflation lumen extending longitudinally therethrough.

26. The apparatus of claim 25 wherein a balloon inflation side tube is connected to, and extends outwardly from, said balloon inflation lumen, to permit infusion of balloon inflation fluid through said balloon inflation lumen.

27. The apparatus of claim 26 further comprising:

a valving apparatus on said balloon inflation side tube.

28. The apparatus of claim 27 wherein said valving apparatus is a slide valve having a Leur connector formed thereon to permit attachment of a syringe thereto.

29. The apparatus of claim 24 wherein said introducer body has a length of less than 30 cm.

30. The apparatus of claim 24 wherein said introducer body has a length of approximately 20 cm.

31. The apparatus of claim 24 wherein said introducer body is substantially cylindrical, and has an outer diameter of 3–12 French.

32. The apparatus of claim 29 wherein said working lumen is substantially cylindrical and has a diameter of approximately 1–10 French.

33. The apparatus of claim 24 wherein said balloon inflation lumen is substantially cylindrical and has a diameter of 0.010–0.020 inches.

34. The apparatus of claim 24 wherein said introducer body comprises an extruded dual-lumen plastic tube having said main lumen and said balloon inflation lumen formed therein in substantially side-by-side relation to one another.

35. The apparatus of claim 34 further comprising a balloon inflation side tube connected to and extending outwardly from said balloon inflation lumen to permit infusion of balloon inflation fluid therethrough.

36. The apparatus of claim 34 further comprising:
a fluid infusion side tube connected to and extending outwardly from said main lumen to permit infusion of fluid therethrough.

37. The apparatus of claim 24 wherein said introducer body is formed of material selected from the group consisting of:
a) Fluropolymer
b) Polyurethane
c) Vinyl
d) Nylon.

38. The apparatus of claim 24 wherein said balloon comprises a cylindrical elastic balloon having a proximal end, a distal end, and a cylindrical mid-portion extending between the proximal and distal ends thereof, said cylindrical elastic balloon being affixed to the outer surface of said introducer body such that balloon inflation fluid may be instilled between said introducer body and the mid-portion of said balloon to cause the mid-portion of said balloon to inflate annularly about said introducer body.

39. The apparatus of claim 38 wherein the mid-portion of said balloon is configured such that, when fully inflated, said balloon has an annular outer diameter of approximately 10–50 cm.

40. A vascular introducer apparatus having an occlusion balloon, said apparatus comprising:
an elongate pliable introducer body insertable into a blood vessel, said introducer body having a proximal end, a distal end, an outer surface and a working lumen extending longitudinally therethrough;
an inflatable occlusion balloon mounted on the outer surface of the introducer body;
a balloon inflation lumen extending through at least a portion of the introducer body to permit infusion of inflation fluid into said balloon;
a hemostasis valving apparatus associated with the working lumen of said introducer apparatus, said valving apparatus comprising a self sealing passageway which will become fully closed and prevent fluid from backflowing out of the proximal end of said working lumen when no elongate object is inserted therethrough, and which will permit insertion of an elongate object through said valving apparatus and through the working lumen of the introducer;
said valving apparatus including a sealing apparatus to seal against a elongate object inserted through said valving apparatus to thereby prevent fluid from backflowing out of the proximal end of said working lumen when an elongate object is inserted therethrough; and
a dilator member insertable through the working lumen of the introducer apparatus, said dilator member having a tapered distal portion which extends beyond the distal end of the introducer apparatus, said dilator member comprising:
i. an elongate member having a proximal end, a distal end, and an outer surface, said tapered distal region being immediately adjacent said distal end thereof;
ii. said dilator member being insertable through said valving apparatus and through the working lumen of the introducer apparatus such that the tapered distal portion of the dilator protrudes beyond the distal end of the introducer apparatus and the valving member forms a seal against the outer surface of the dilator member; and
a guidewire lumen extending longitudinally through said dilator member.

41. The apparatus of claim 40 wherein said introducer body is a dual lumen tube having said working lumen and said balloon inflation lumen extending longitudinally therethrough.

42. The apparatus of claim 41 wherein a balloon inflation side tube is connected to, and extends outwardly from, said balloon inflation lumen, to permit infusion of balloon inflation fluid through said balloon inflation lumen.

43. The apparatus of claim 42 further comprising:
a valving apparatus on said balloon inflation side tube.

44. The apparatus of claim 43 wherein said valving apparatus is a slide valve having a Leur connector formed thereon to permit attachment of a syringe thereto.

45. The apparatus of claim 40 wherein said introducer body has a length of less than 30 cm.

46. The apparatus of claim 40 wherein said introducer body has a length of approximately 20 cm.

47. The apparatus of claim 40 wherein said introducer body is substantially cylindrical, and has an outer diameter of 3–12 French.

48. The apparatus of claim 45 wherein said working lumen is substantially cylindrical and has a diameter of approximately 1–10 French.

49. The apparatus of claim 40, wherein said balloon inflation lumen is substantially cylindrical and has a diameter of 0.010–0.020 inches.

50. The apparatus of claim 40 wherein said introducer body comprises an extruded dual-lumen plastic tube having said main lumen and said balloon inflation lumen formed therein in substantially side-by-side relation to one another.

51. The apparatus of claim 50 further comprising a balloon inflation side tube connected to and extending outwardly from said balloon inflation lumen to permit infusion of balloon inflation fluid therethrough.

52. The apparatus of claim 50 further comprising:
a fluid infusion side tube connected to and extending outwardly from said main lumen to permit infusion of fluid therethrough.

53. The apparatus of claim 40 wherein said introducer body is formed of material selected from the group consisting of:
a) Fluropolymer
b) Polyurethane
c) Vinyl
d) Nylon.

54. The apparatus of claim 40 wherein said balloon comprises a cylindrical elastic balloon having a proximal end, a distal end, and a cylindrical mid-portion extending between the proximal and distal ends thereof, said cylindrical elastic balloon being affixed to the outer surface of said introducer body such that balloon inflation fluid may be instilled between said introducer body and the mid-portion of said balloon to cause the mid-portion of said balloon to inflate annularly about said introducer body.

55. The apparatus of claim 54 wherein the mid-portion of said balloon is configured such that, when fully inflated, said balloon has an annular outer diameter of approximately 10–50 cm.

56. The apparatus of claim 40 wherein said valving apparatus is incorporated into a valving assembly mounted on the proximal end of said introducer body.

57. The apparatus of claim 56 wherein said valving assembly comprises:
said valving apparatus;
an end cap mounted over said valving apparatus, said end cap having a proximal opening formed therein, the proximal opening of said end cap being in alignment with the self-sealing passageway of said valving apparatus such that an elongate object may be inserted through said proximal opening, of the end cap, through the self-sealing passageway of said valving apparatus, and through the main lumen of said introducer body.

58. The apparatus of claim 57, wherein said valving assembly further comprises:

a gripping apparatus operative to frictionally engage and hold an elongate object inserted through said introducer apparatus.

59. The apparatus of claim 58 wherein said gripping apparatus comprises:

a compressible gripping ring mounted in alignment with the proximal opening of said end cap such that, when said end cap is tightened, said gripping ring will be compressed.

60. The apparatus of claim 59 further comprising first and second rigid washers positioned on opposite sides of said gripping ring such that when said end cap is tightened, said gripping ring will be compressed between said washers.

* * * * *